US012758795B2

(12) United States Patent
Jalalifar et al.

(10) Patent No.: US 12,758,795 B2
(45) Date of Patent: Oct. 13, 2026

(54) SYSTEM AND METHODS FOR AUTOMATIC ASSESSMENT OF RADIOTHERAPY OUTCOME IN TUMOURS USING LONGITUDINAL TUMOUR SEGMENTATION ON SERIAL MRI

(71) Applicants: Sunnybrook Research Institute, Toronto (CA); Seyed Ali Jalalifar, Toronto (CA); Ali Sadeghi-Naini, Toronto (CA)

(72) Inventors: Seyed Ali Jalalifar, Toronto (CA); Ali Sadeghi-Naini, Toronto (CN); Hany Soliman, Toronto (CA); Arjun Sahgal, Toronto (CA)

( * ) Notice: Subject to any disclaimer, the term of this patent is extended or adjusted under 35 U.S.C. 154(b) by 0 days.

(21) Appl. No.: 18/875,499

(22) PCT Filed: Jun. 16, 2023

(86) PCT No.: PCT/CA2023/050840
§ 371 (c)(1),
(2) Date: Dec. 16, 2024

(87) PCT Pub. No.: WO2023/240363
PCT Pub. Date: Dec. 21, 2023

(65) Prior Publication Data
US 2025/0325837 A1 Oct. 23, 2025

Related U.S. Application Data

(60) Provisional application No. 63/352,881, filed on Jun. 16, 2022.

(51) Int. Cl.
*A61N 5/10* (2006.01)
*G01R 33/56* (2006.01)
(Continued)

(52) U.S. Cl.
CPC ....... *A61N 5/1039* (2013.01); *G01R 33/5608* (2013.01); *G16H 20/40* (2018.01);
(Continued)

(58) Field of Classification Search
CPC .......... A61N 5/1039; A61N 2005/1055; G01R 33/5608; G01R 33/4808; G16H 20/40;
(Continued)

(56) References Cited

U.S. PATENT DOCUMENTS

2010/0182006 A1* 7/2010 Yang .................... G01R 33/561 324/309
2016/0275676 A1* 9/2016 Thiele ........................ G06T 7/50
(Continued)

FOREIGN PATENT DOCUMENTS

IN 3655/DEL/2015 5/2017
KR 20200120311 A 10/2020
KR 20210147765 A 12/2021

OTHER PUBLICATIONS

Yu et al (Stereotactic Body Radiation Therapy Versus Intensity-Modulated Radiation Therapy for Prostate Cancer: Comparison of Toxicity, Journal of Clinical Oncology, 32(12), 1195-1201, 2014) (Year: 2014).*
(Continued)

*Primary Examiner* — Alexei Bykhovski
(74) *Attorney, Agent, or Firm* — Gerald W. Roberts; Dentons Bingham Greenebaum LLP

(57) ABSTRACT

A system for automatic assessment of therapy outcome in cancer patients treated with radiation therapy, the system comprising a machine-learning-based segmentation model for delineating tumours longitudinally in serial magnetic resonance imaging (MRI) with high precision. Longitudinal segmentations of tumour before and/or during treatment and/or at multiple follow-up sessions after the radiation therapy permits monitoring changes in tumour size and is used in the system for automatic assessment of therapy outcome based on standard clinical criteria.

28 Claims, 6 Drawing Sheets

(51) Int. Cl.
*G16H 20/40* (2018.01)
*G16H 30/40* (2018.01)
*G16H 50/20* (2018.01)
*G16H 70/20* (2018.01)

(52) U.S. Cl.
CPC ............. *G16H 30/40* (2018.01); *G16H 50/20* (2018.01); *G16H 70/20* (2018.01); *A61N 2005/1055* (2013.01)

(58) Field of Classification Search
CPC ........ G16H 30/40; G16H 50/20; G16H 70/20; A61B 5/0042; A61B 5/4836; A61B 2576/026; A61B 5/4064; A61B 5/4842; A61B 5/7267; A61B 5/055
See application file for complete search history.

(56) References Cited

U.S. PATENT DOCUMENTS

| | | | | |
|---|---|---|---|---|
| 2023/0083261 | A1* | 3/2023 | Reyes .................. | A61B 5/0042 382/131 |
| 2025/0174353 | A1* | 5/2025 | Sadeghi-Naini ..... | G06N 3/0985 |

OTHER PUBLICATIONS

Andy Wong (Authorized Officer), International Search Report, International Application No. PCT/CA2023/050840, mailed Aug. 18, 2023, 3 pages total, Canadian Intellectual Property Office, Gatineau, Quebec.

Andy Wong (Authorized Officer), Written Opinion of the International Searching Authority, International Application No. PCT/CA2023/050840, mailed Aug. 18, 2023, 5 pages total, Canadian Intellectual Property Office, Gatineau, Quebec.

Cecile Chatel (Authorized Officer), Notification Concerning Transmittal of International Preliminary Report on Patentability, International Application No. PCT/CA2023/050840, mailed Dec. 26, 2024, 7 pages total (including International Preliminary Report on Patentability and Written Opinion of the International Searching Authority), The International Bureau of WIPO, Geneva, Switzerland.

European Patent Office Examiner Tibrewal-Fabricius, extended European search report (including supplementary European search report and including European search opinion), European Patent Application 23822584.1, May 27, 2026, 9 pages, European Patent Office, Munich, Germany.

Jungheum Cho, et al., "Deep Learning-Based Computer-Aided Detection System for Automated Treatment Response Assessment of Brain Metastases on 3D Mri," Frontiers in Oncology, Oct. 2, 20217; 11:739639, 10 pages.

Nancy U. Lin, et al., "Response assessment criteria for brain metastases: proposal from the RANO group," The Lancet Oncology, vol. 16, Jun. 2015, pp. e270-278.

Ken Chang, et al., "Automatic assessment of glioma burden: a deep learning algorithm for fully automated volumetric and bidimensional measurement," Neuro-Oncology, vol. 21, Issue 11, Advance Access Date Jun. 13, 2019, pp. 1412-1422.

Hans-Christian Bauknecht, et al., "Effect of MRI-based semiautomatic size-assessment in cerebral metastases on the RANO-BM classification," Clin Neuroradiol (2020), Jun. 13, 2019, vol. 30, No. 2, pp. 263-270.

* cited by examiner

10

SYSTEM AND METHODS FOR AUTOMATIC ASSESSMENT OF RADIOTHERAPY OUTCOME IN TUMOURS USING LONGITUDINAL TUMOUR SEGMENTATION ON SERIAL MRI

FIELD

The present disclosure relates to automatic monitoring and evaluation of radiotherapy outcome.

BACKGROUND

About 10% to 30% of all cancer patients develop brain metastasis [1], with a higher risk for melanoma, lung, and breast cancer patients. The annual estimated incidence of brain metastases in the United States exceeds 14 persons per 100,000 based on population studies [2]. Brain metastasis may occur as a single tumour (approximately 29% of cases), two-three tumours (35% of cases), and more than three tumours (36% of cases) [3]. Metastatic brain tumours represent a major cause of morbidity and mortality in cancer patients. Whereas a significant proportion of cancer patients survive for many years if the cancer is identified at an early stage while it is still localized [4], when the tumour is metastasized to the brain, the median survival ranges from as short as 5 months to up to 4 years, based on the subgroup and origin of the cancer [5]-[8]. Early diagnosis and precise treatment of brain metastasis may lead to the reduction of brain symptoms and may enhance the quality of life and survival of the patients.

Treatment planning for patients diagnosed with brain tumours depends on many factors including the origin of cancer, symptoms, number of metastases, and location of the tumour. Two main treatment modalities available for management of the brain tumours include surgery and radiation therapy. Surgery involves resection of the tumour and is often administered when the tumour is large and accessible. Other contributing factors are patient's age, presence of other extracranial diseases, and relative proximity to eloquent brain areas [9]. In whole brain radiation therapy (WBRT) the prescribed radiation dose is delivered to the whole brain in many low-dose fractions over several weeks [10]. In stereotactic radiosurgery (SRS) and hypo-fractionated stereotactic radiotherapy (SRT), a high-dose of radiation is delivered to a precisely targeted area to minimize injury to the neighboring regions. Whereas in SRS, the prescribed radiation dose is delivered in a single fraction, in SRT the total radiation dose is delivered in very few fractions over few days.

Magnetic resonance imaging (MRI) is the main imaging modality for diagnosis, treatment planning, and therapy outcome evaluation of brain tumours. MRI scans are acquired before (baseline) and at multiple follow-up sessions after the radiation therapy as part of the standard treatment planning and outcome assessment procedure. The procedure requires accurate delineation of the tumour that is often performed by expert radiation oncologists and neuroradiologists. Evaluation of radiotherapy outcome of brain tumours on serial MRI is mainly performed based on the standard criteria presented by the response assessment in neuro-oncology (RANO) group [11]. The RANO criteria are principally based on changes in the longest diameter of the target tumour in the axial, coronal, and sagittal planes compared to baseline or nadir (smallest tumour size on the previous scans) to specify its response to therapy. The four categories of therapy response based on the RANO criteria include complete response (no target tumour remaining), partial response (more than X % reduction in the longest diameter or the product of two longest perpendicular diameters compared to baseline), minor response, stable disease (less than X % decrease compared to baseline but also less than Y % increase in the longest diameter or the product of two longest perpendicular diameters compared to nadir), or progressive disease (also referred to as local failure; more than Y % increase in the longest diameter or the product of two longest perpendicular diameters compared to nadir); where X and Y are determined based on the tumour type. Tumour enlargement on MRI after radiotherapy may also become apparent due to adverse radiation effect (ARE). Such evident tumour enlargements on MRI often become stable or followed by a decrease in tumour size on subsequent imaging follow-ups. Differentiating between tumour progression and ARE is crucial for radiotherapy response evaluation. The standard approaches to diagnose ARE include serial MRI (including the use of T1-weighted, T2-weighted, and perfusion imaging), and where applicable, histology on resected specimens [13]-[15].

In order to calculate the tumour size changes on serial imaging, precise delineation of tumour is required for each imaging session. Manual segmentation of tumour on volumetric images acquired at several follow-up sessions for each patient is a tedious and time-consuming job. An automatic and robust tumour segmentation framework is highly desirable in clinic and could streamline radiation therapy outcome evaluation workflow considerably. Because of many applications of automatic tumour segmentation, intense research has been carried out on this topic [16]-[18]. The existing segmentation algorithms include those that apply traditional methods such as region-based [19], [20] and model-based techniques [21], with more recent methodologies based on deep neural networks [22]-[24]. Deep learning-based image segmentation is now very popular in the literature and has been demonstrated to outperform the traditional methods [25]-[27]. The deep networks for image segmentation generally consist of stacked convolutional layers and occasionally fully connected layers. Among many networks introduced for the task of segmentation, 2D and 3D UNet gained widespread popularity because of their robustness on different modalities [26], [28]. However, 2D UNet has the drawback of extracting similar features multiple times throughout the network in addition to inefficient modeling of long-range spatial dependencies. A main limitation associated with 3D UNet is that it often cannot handle large input sizes due to memory limitations with the complex architecture of the network.

The standard clinical approach to assess the radiotherapy outcome of brain tumours is through monitoring the changes in tumour size on longitudinal MRI. This assessment requires contouring the tumour on many volumetric images acquired before and at several follow-up scans after the treatment that is routinely done manually by oncologists with a substantial burden on the clinical workflow.

SUMMARY

In one of its aspects, a method and system for automatic monitoring and evaluation of radiotherapy outcome comprising a machine-learning-based segmentation framework for automatic assessment of radiation therapy outcome of brain tumours using MRI.

In another aspect, a system for automatic assessment of therapy outcome in cancer patients treated with radiation therapy, the system comprising:

an imaging system for acquiring a series of input images comprising a region of interest (ROI) comprising a tumour, wherein each of the input images in the series is acquired from the same subject in different imaging sessions before, during and/or after radiation therapy;

a computer system comprising a hardware processor and a memory device on which instructions are encoded to cause the hardware processor to perform the operations of;

with a machine-learning-based segmentation framework comprising one or more deep neural networks in cascade and/or parallel configurations, generating at least a tumour mask as the final output of the segmentation framework for each input image in the series;

calculating and reporting dimensions of the tumour in various directions;

using the calculated tumour dimensions, identifying and reporting a tumour size status;

using the calculated tumour dimensions, categorizing and reporting the tumour size change at each mentioned imaging session into categories comprising at least one of shrinkage, steady and enlargement, based on a predefined criteria comprising at least a response assessment in neuro-oncology (RANO) criteria;

using a pattern of tumour-size-change categories, assessing and reporting the radiation therapy outcome.

In another aspect, a method for automatic assessment of therapy outcome in cancer patients treated with radiation therapy, the method comprising:

with an imaging system, acquiring a series of input images comprising a region of interest (ROI) comprising a tumour, wherein each of the input images in the series are acquired from the same subject in different imaging sessions before, during and/or after radiation therapy;

with a machine-learning-based segmentation framework comprising one or more deep neural networks in cascade and/or parallel configurations, generating at least a tumour mask as the final output of the segmentation framework for each input image in the series;

calculating and reporting dimensions of the tumour in various directions;

using the calculated tumour dimensions, identifying and reporting a tumour size status;

using the calculated tumour dimensions, categorizing and reporting the tumour size change at each mentioned imaging session into categories comprising at least one of shrinkage, steady and enlargement, based on a predefined criteria comprising at least a response assessment in neuro-oncology (RANO) criteria;

using a pattern of tumour-size-change categories, assessing and reporting the radiation therapy outcome.

In another aspect, a computer readable medium storing instructions executable by a processor to carry out the operations comprising:

receiving a series of input images comprising a region of interest (ROI) comprising a tumour, wherein each of the input images in the series are acquired from the same subject in different imaging sessions before, during and/or after radiation therapy;

with a machine-learning-based segmentation framework comprising one or more deep neural networks in cascade and/or parallel configurations, generating at least a tumour mask as the final output of the segmentation framework for each input image in the series;

calculating and reporting dimensions of the tumour in various directions;

using the calculated tumour dimensions, identifying and reporting a tumour size status;

using the calculated tumour dimensions, categorizing and reporting the tumour size change at each imaging session into categories comprising at least one of shrinkage, steady and enlargement, based on a predefined criteria comprising at least a response assessment in neuro-oncology (RANO) criteria;

using a pattern of tumour-size-change categories, assessing and reporting the radiation therapy outcome.

Advantageously, there is provided a framework for automatic segmentation of brain tumours that are planned for radiation therapy, which uses deep-learning techniques to delineate tumours before and/or during radiotherapy, and/or at multiple imaging follow-ups after the radiotherapy, to assess the therapy outcome automatically based on some pre-defined criteria such as the RANO criteria. The framework comprises a deep learning-based segmentation model to delineate tumours longitudinally on serial MRI with substantially high precision. Longitudinal changes in tumour size are then analyzed automatically to assess the local response and detect possible adverse radiation effects (ARE) after radiation therapy.

As an example, the segmentation framework may employ a cascade of two 2D UNets to find the approximate position of the tumour and decrease the size of the input volume while substantially minimizing loss of any information for tumour segmentation. The cropped volume may then be fed into a 3D UNet to generate a volumetric segmentation mask. The cropped images may also be fed into a multi-scale attention-guided network to generate a complementary set of 2D masks. At the end, the outputs of these two networks may be fused to generate the final 3D tumour mask. The results demonstrate a very good accuracy of this exemplary framework in segmenting brain tumours on MRI, and has better performance compared to the 2D and 3D UNets and their cascade. Results of automatic therapy outcome evaluation with this exemplary framework demonstrate a very good agreement to the manual assessments by expert clinicians with an accuracy, sensitivity, and specificity of 91%, 89%, and 92% in detecting local control/failure and 91%, 100%, and 89% in detecting ARE on an independent test set. The comparison between automatic therapy outcome evaluation using this exemplary framework and manual assessments by expert oncologists demonstrates a good agreement with an accuracy, sensitivity, and specificity of 91%, 89%, and 92%, respectively, in detecting local control/failure and 91%, 100%, and 89% in detecting ARE on the independent test set.

Furthermore, the method and system streamline the radiotherapy outcome evaluation workflow and makes serial tumour segmentation, and consequently the therapy outcome evaluation, more consistent in the clinic.

DETAILED DESCRIPTION

Figure 1:
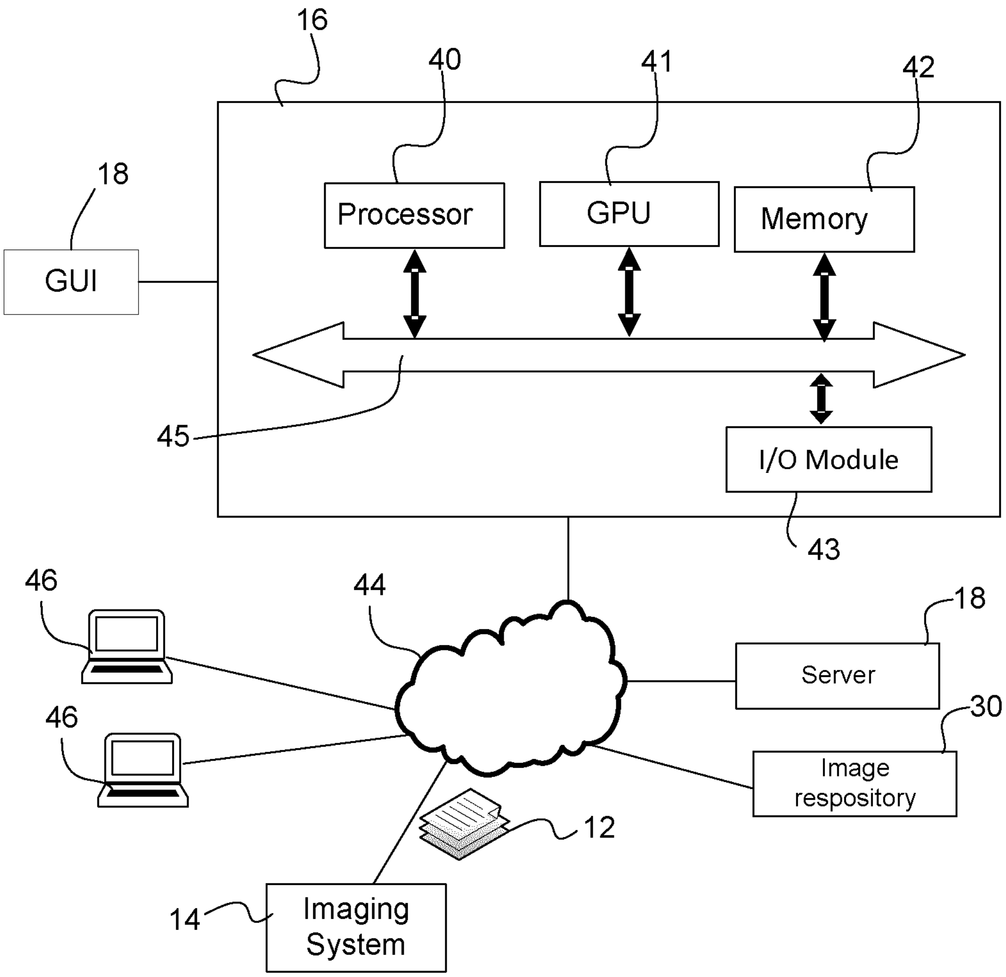
FIG. 1 shows a top-level diagram of an overall system architecture for automatic assessment of radiation therapy outcome of brain tumours using MRI.

The following detailed description refers to the accompanying drawings. Wherever possible, the same reference numbers are used in the drawings and the following description to refer to the same or similar elements. While embodiments of the disclosure may be described, modifications, adaptations, and other implementations are possible. For example, substitutions, additions, or modifications may be made to the elements illustrated in the drawings, and the methods described herein may be modified by substituting, reordering, or adding stages to the disclosed methods. Accordingly, the following detailed description does not limit the disclosure. Instead, the proper scope of the disclosure is defined by the appended claims.

Moreover, it should be appreciated that the particular implementations shown and described herein are illustrative of the invention and are not intended to otherwise limit the scope of the invention in any way. Indeed, for the sake of brevity, certain sub-components of the individual operating components, and other functional aspects of the systems may not be described in detail herein. Furthermore, the connecting lines shown in the various figures contained herein are intended to represent exemplary functional relationships and/or physical couplings between the various elements. It should be noted that many alternative or additional functional relationships or physical connections may be present in a practical system.

Referring to FIG. 1, there is shown a top-level diagram of an overall system architecture 10 for automatic assessment of radiotherapy outcome, for example, in brain tumours using MRI. In one example, images 12, such as those with brain tumours, are acquired from one or more imaging systems 14 and may comprise medical imaging equipment such as an X-ray imaging system, a CT scan imaging system, an ultrasound imaging system, an MRI imaging system, a nuclear medicine imaging system, and so forth. The images 12 of brain tumours captured by the one or more imaging systems 14 are rendered as a digital representation and stored in a computing device 16. The computing device 16 may comprise one or more processing units, such as, graphics processing units (GPUs). In one example, the computing device 16 implements a deep learning-based segmentation model to delineate tumours longitudinally on serial MRI with high precision, and longitudinal changes in tumour size are then analyzed automatically to assess the local response and detect possible adverse radiation effects (ARE) after radiotherapy, with the results being output via a graphical user interface 18.

The computing device 16 comprises an image repository 30 for storage of the images 12. The image repository 30 may be computer readable medium e.g. a hard disk. Alternatively, the acquired images 12 may be stored on a storage server or a cloud computing server. The image repository 30 may also include images of patients for analysis, and/or training images that have been previously analyzed and/or annotated.

The term computing device refers to data processing hardware and encompass all kinds of apparatus, devices, and machines for processing data, including by way of example, a programmable processor, a computer, or multiple processors or computers. The apparatus can also be, or further include, special purpose logic circuitry, e.g., a central processing unit (CPU) 40, a GPU 41 graphics processing unit); a FPGA (field programmable gate array), or an ASIC (application-specific integrated circuit). In some implementations, the data processing apparatus and/or special purpose logic circuitry may be hardware-based and/or software-based. The apparatus can optionally include code that creates an execution environment for computer programs, e.g., code that constitutes processor firmware, a protocol stack, a database management system, an operating system, or a combination of one or more of them. Although a single CPU 40 is illustrated in FIG. 1, two or more processing units may be used according to particular needs, desires, or particular implementations of the computing device 16. In one example, a GPU 41 is implemented to accelerate computations pertaining to the deep learning methodology. Generally, the GPU 41 executes instructions and manipulates data to perform the operations of the computing device 16.

Memory 42 stores data for the computing device 16 and/or other components of the system 10. Although illustrated as a single memory 42 in FIG. 1, two or more memories may be used according to particular needs, desires, or particular implementations of the computing device 16. While memory 42 is illustrated as an integral component of the computing device 16 in alternative implementations, memory 42 can be external to the computing device 16 and/or the system. For example, memory 42 comprises computer-readable media (transitory or non-transitory, as appropriate) suitable for storing computer program instructions and data include all forms of non-volatile memory, media and memory devices, including by way of example semiconductor memory devices, e.g., erasable programmable read-only memory (EPROM), electrically erasable programmable read-only memory (EEPROM), and flash memory devices; magnetic disks, e.g., internal hard disks or removable disks; magneto-optical disks; and CD-ROM, DVD+/−R, DVD-RAM, DVD-ROM disks and Blu-ray disks. The memory 42 may store various objects or data, including caches, classes, frameworks, applications, backup data, jobs, web pages, web page templates, database tables, repositories storing business and/or dynamic information, and any other appropriate information including any parameters, variables, algorithms, models, instructions, rules, constraints, or references thereto. Additionally, the memory may include any other appropriate data, such as logs, policies, security or access data, reporting files, as well as others. The processor 40 and the memory 42 can be supplemented by, or incorporated in, special purpose logic circuitry.

In one example, an application in memory 42 comprises algorithmic instructions providing functionality according to particular needs, desires, or particular implementations of the computing device 16, particularly with respect to functionality required for delineating tumours longitudinally on serial MRI with high precision, and automatically analyzing longitudinal changes in tumour size to assess the local response and detect possible adverse radiation effects (ARE), e.g. after radiotherapy.

The computing device 16 may comprise an input/output module 43, to which an input device, such as a keypad, key board, touch screen, microphone, speech recognition device, other devices that can accept user information, and/or an output device that conveys information associated with the operation of the computing device 16, including digital data, visual and/or audio information, or the GUI 18.

The computing device 16 comprises an interface, as part of the I/O module 43, used according to particular needs, desires, or particular implementations of the computing device 16. The interface is used by computing device 16 for communicating with other systems in a distributed environment, connected to network 44. Generally, the interface comprises logic encoded in software and/or hardware in a suitable combination and operable to communicate with the network 44. More specifically, the interface may comprise software supporting one or more communication protocols associated with communications. The various components of the computing system are connected by an interconnections means 45, such as an address bus, data bus, a control bus and a peripheral bus.

Client terminals 46 (e.g., remotely located radiology workstations) may request services related to automatic monitoring and evaluation of radiotherapy outcome, for example, in brain tumours and access the results over the communications network 44. Accordingly, the computing device 16 may provide software as a service (Saas) to the client terminals 46, or provide an application for local download to the client terminals 46, and/or provide functions using a remote access session to the client terminals 46, such as through a web browser. Accordingly, the assessments may be accessible for clinicians on an on-demand basis from the client terminals 46. System 10 may also comprise data storage 47, which is configured to maintain one or more datasets, including data structures storing linkages and other data, such as medical images, libraries, models and rules. Data storage 47 may be a relational database, a flat data storage, a non-relational database, among others.

Data Acquisition and Pre-Processing

In one study, imaging and clinical data were collected from 116 patients (152 tumours; average size: 2.4±1.0 cm) diagnosed with brain metastasis and treated with hypofractionated SRT. The imaging data included gadolinium-contrast-enhanced T1-weighted and T2-weighted-fluid-attenuation-inversion-recovery (T2-FLAIR) images acquired before treatment (baseline) and at up to 9 follow-ups after the treatment. The dataset also included treatment-planning gross tumour volume (GTV) contours for each patient that were used to generate ground truth tumour masks at baseline and the first follow-up under supervision of expert oncologists. The in-plane image resolution and the slice thickness were 0.5 and 1.5 mm for T1-weighted and 0.5 and 5 mm for T2-FLAIR images, respectively. All images were resampled with a voxel size of 0.5×0.5×1 mm3. The voxel intensities in each image were normalized to be between 0) and 1. The T2-FLAIR images were co-registered on their corresponding T1-weighted images using an affine registration. Among the 116 patients, 96 patients (130) tumours) were randomly selected for training and optimizing the models for automatic radiotherapy outcome assessment in brain malignancies, and the remaining 20 patients (22 tumours) were kept as an unseen test set for independent evaluation.

The tumours were monitored longitudinally after SRT and the pattern of changes in tumour size as well as the ground truth local control/failure (LC/LF) outcome for each tumour was determined by a radiation oncologist using the follow-up imaging data. The ground truth tumour size status (decease/stable/increase) was determined for each follow-up scan. Specifically, the tumour size status was determined as decrease/increase if a measurable (≥2 mm) decrease/increase was evident in the longest diameter of the tumour in the axial plane compared to the previous scan, otherwise it was determined as stable. The RANO criteria for brain metastasis (RANO-BM criteria) were used to determine an outcome of LC (complete response, partial response, or stable disease) or LF (progressive disease) for each tumour [11]. Local progression was differentiated from adverse radiation effect (ARE) based on the report by Sneed et al. [13]. All cases of ARE were diagnosed based on serial imaging (including the use of perfusion MRI), and/or histological confirmation [14].

Tumour Segmentation Framework

Figure 2A:
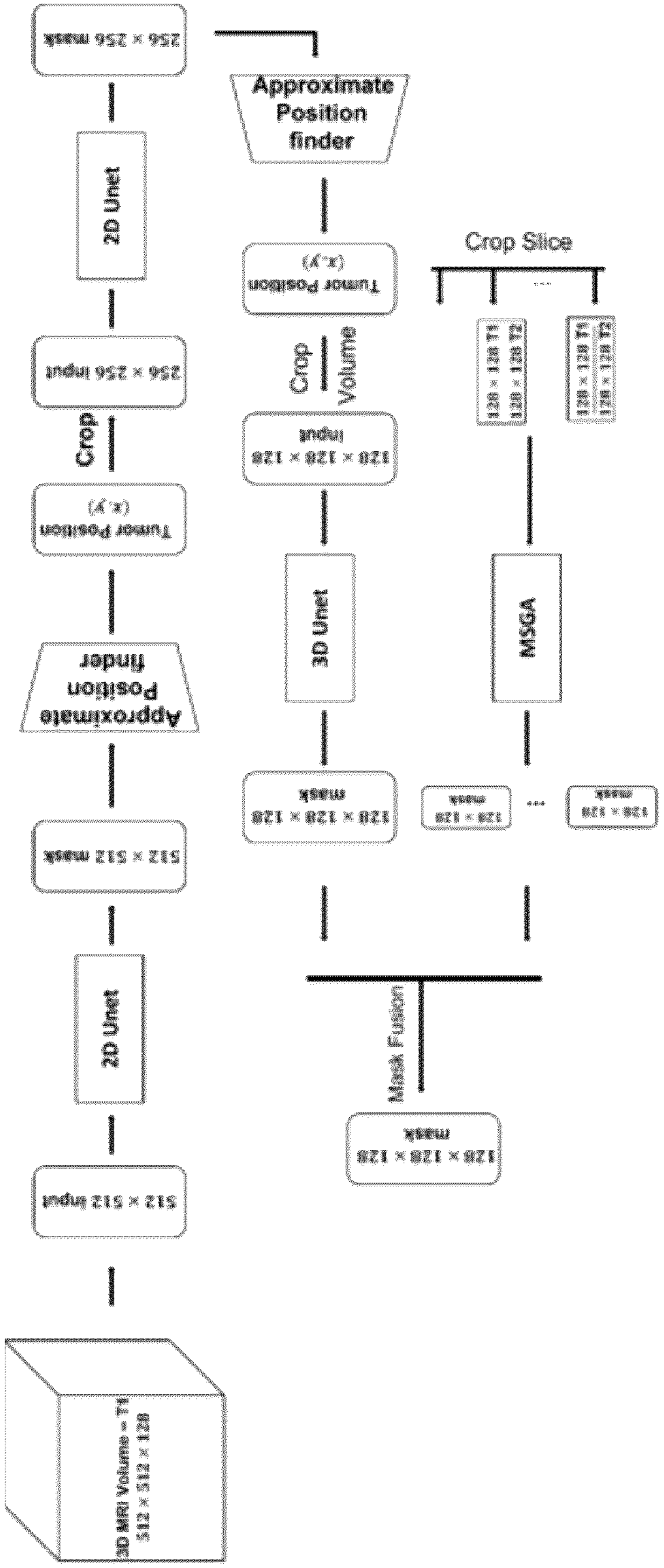
FIG. 2*a* shows a flowchart outlining components of an exemplary framework for automatic tumour segmentation on MRI.
Figure 2B:
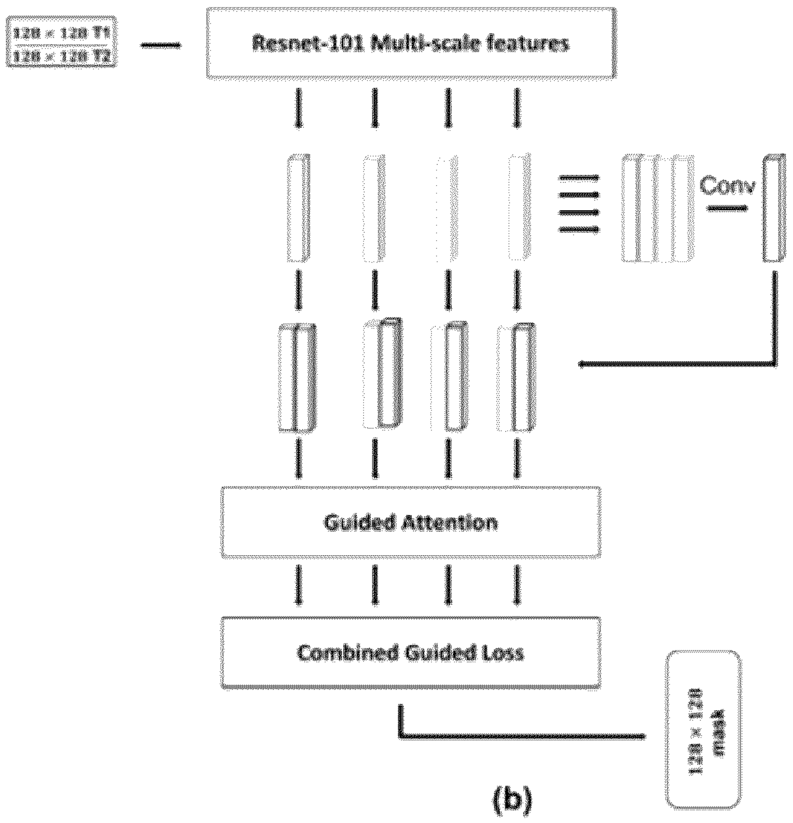
FIG. 2*b* shows a multi-scale self-guided attention (MSGA) network structure.

FIGS. 2*a* and 2*b* show a scheme of the exemplary framework implemented and applied in the study mentioned in [0032] for automatic segmentation of brain tumours on MRI. In more detail, the framework comprises two cascaded 2D UNets to find the approximate position of the tumour. Once the approximate tumour position is found, the image is cropped around the tumour to make the size of input image smaller for the next network. Specifically, the size of input T1-weighted images for the first and second 2D UNets is 512×512 and 256×256 pixel, respectively. The need for cropping images stems from the fact the both the 3D UNet and multi-scale self-guided attention (MSGA) network [29] adapted in the framework have memory limitation which makes their training process challenging. If the input size for the 3D UNet is the original image size (512×512×128 voxel) without cropping, one needs to patch or resize the input volume to meet the memory limitations of the network. FIG. 2*b* shows a MSGA network structure, in which features extracted at different scales from Resnet-101 are concatenated and convolved and then self-concatenated and fed into guided attention module, and the resulting self-guided features are fed into the guided loss. Patching the volume leads to lose contextual information (e.g., tumour tears apart in different patches) while resizing it results in losing detailed local information. Similarly, and due to its complex architecture, training the MSGA network on the original 2D images (512×512 pixel) with two channels of T1-weighted and T2-FLAIR requires limiting the batch size substantially. With cropping, it is possible to preserve both local and contextual information using the approximate position of the tumour estimated with the cascaded 2D UNets. The output of each 2D UNet for a patient is a set of 128 2D masks with size of 512×512 pixel for the first and 256×256 pixel for the second 2D UNet. To find the approximate position of the tumour from these masks, a logical OR operation is applied on all the 2D masks to create a single mask presenting an upper-bound of the tumour areas in different slices. Subsequently, the connected components are identified in the single mask and the center of each connected component is regarded as the approximate center of the corresponding tumour. The approximated centers are used to crop the image around the tumour region. In cases where there is more than one tumour in an MRI volume, the tumours are treated separately, and the final masks are fused at the end. At the core of the framework in this disclosure are two segmentation networks including a 3D UNet and a MSGA network. The 3D UNet is fed with the cropped T1-weighted volumetric images (128×128×128 voxel), and the MSGA network is fed with cropped two-channel T1-weighted and T2-FLAIR image slices (128×128 pixel). The output of these two networks is fused at the end using a slice-wise averaging over their output probability maps. In one example, the final output masks are generated by thresholding the averaged probability maps with a threshold level of 0.5.

The use of a combination of 2D UNet, 3D UNet, and MSGA network takes advantage of their features, while simultaneously mitigating their limitations. The desirable performance of the 2D UNet architecture in various segmentation tasks is due, in part, to its capability to capture context and enable localization, using a contracting path and a symmetric expanding path, with skip connections in between the two paths [28]. Such architecture enables the network to share features from multiple lavers and overcome the trade-off between localization accuracy and the context utilization. The drawback of 2D UNet, however, is that it does not consider the 3D spatial dependencies between the voxels, and consequently, loses a considerable amount of useful information for segmentation. To overcome this, Çiçek et al. proposed the 3D UNet as a volumetric image segmentation network [26], which maintains the benefits of the 2D UNet architecture but also considers the voxel dependencies. Considering 3D spatial dependencies comes at the cost of high memory consumption because of the huge input size. A cascaded network of 2D UNet and 3D UNet benefits from the advantages of 3D UNet while the redundant information can be filtered out using 2D UNet to meet the memory limitations of the 3D UNet. The two main draw backs of the encoder-decoder architectures such as 2D and 3D UNet includes deriving redundant information, and more importantly, inefficient modeling of long-range feature dependencies in these networks. Sinha et al. [29] proposed a multi-scale self-guided attention network to overcome these limitations. The MSGA network enables capturing richer contextual dependencies and neglect irrelevant information by using an attention mechanism. Also, utilization of interdependent channel maps which enables the network to integrate local features with their corresponding global dependencies makes it efficient in our application, where the network is fed with two channels of T1-weighted and T2-FLAIR images.

Training and Evaluation of the Framework

In order to train and evaluate the tumour segmentation framework, the data associated with samples of the training data set and test data sets were completely separated at patient level. The networks in the framework were trained independently using the data acquired from the training samples. The second 2D UNet, the 3D UNet, and the MSGA network were trained using the manually cropped data from the training set. The networks were only trained on the images acquired at baseline. The framework was initially evaluated in terms of segmentation accuracy, using the images of the independent test set acquired at the baseline and the first follow-up. The Dice similarity coefficient, Hausdorff distance, and the tumour volume estimation error were used for this evaluation. The performance of the framework was subsequently evaluated in monitoring the tumour size status after SRT and automatic assessment of therapy outcome using the imaging data of the independent test set acquired at the baseline and all the follow-ups available for each patient. For comparison, all experiments were conducted using four different models following a similar training and evaluation procedure. The first model included two cascaded 2D UNets, whereas the second model consisted of a 3D UNet. Because of the memory limitations, for training the 3D UNet model a manual cropping of 128×128×128 voxel was done around each tumour within the 3D image. For testing, however, each 512×512×128 voxel volume was patched into 16 input patches of 128×128×128 voxel and the associated masks were concatenated together at the end. The third model included two cascaded 2D UNets followed by a 3D UNet, and the fourth model incorporated the complete framework in this study (FIGS. 2*a-b*). Pre-training of the networks for weight initialization was performed using the data from the brain tumour segmentation (BraTS) dataset [30]. A set of 9) tumours from the training samples was used as the validation set for tuning the network hyper parameters in the training phase. A batch size of four (4) was used for training the 2D UNets, while the batch size for the 3D UNet and MSGA network was set to one because of the memory limitations. The training was performed with a learning rate of 0.0001 for all networks, and with the Dice similarity coefficient and cross entropy as the loss function for the 2D and 3D UNets, respectively.

Procedure and Criteria for Automatic Assessment of Tumour Size Status, Local Response, and ARE Outcome The segmentation masks generated by the deep learning models were used to estimate the size of tumour in each scan and, subsequently, the tumour size changes after SRT. The tumour size status, local response, and ARE outcome were then assessed automatically based on the estimated changes in tumour size using the procedure and criteria described below.

A typical SRT outcome evaluation workflow in the clinic consists of determining the tumour size status at each follow-up scan compared to the previous scan. For automatic assessment of tumour size status, following the protocol applied in clinic, the longest diameter of tumour in axial plane was calculated for all scans using the automatic segmentation masks. Tumour size status at each follow-up scan was labeled as increase or decrease if a measurable increase or decrease (≥2 mm) was estimated, respectively, in the tumour's longest diameter compered to the previous scan. Otherwise, it was labeled as stable. The tumour size status labels identified automatically were compared with the ground truth labels to evaluate the performance of automatic labeling in terms of accuracy, precision and recall. It should be noted that this step was only to evaluate the performance of the network in automatic labeling of tumour size status and not the local response (discussed below).

The SRT outcome in terms of LC/LF and ARE was evaluated for each tumour automatically based on the RANO-BM criteria. Using the automatic segmentation masks, the longest diameter of tumour in axial, coronal and sagittal planes was estimated for the baseline and all follow-ups. The relative change in the longest diameter of tumour was calculated at each follow-up compared to the baseline and nadir. The change in the tumour size at each follow-up was categorized into three categories of shrinkage, steady, and enlargement when more than 30% decrease compared to baseline, less than 30% decrease compared to baseline but also less than 20% increase compared to nadir, and more than 20% increase compared to nadir was detected in the tumour longest diameter, respectively [12]. The shrinkage/steady/enlargement patterns determined for each tumour at the follow-up scans were used for automatic detection of LC/LF and ARE outcome. Any tumour demonstrating a sequence of steady or shrinkage patterns at follow-ups with no enlargement was classified with an LC outcome. When an enlargement was detected in the pattern of size changes, the relative change in the tumour longest dimeter at the next follow-up was calculated compared to the scan in which the enlargement was detected. The tumour was classified with an LF outcome if its size increased again (more than 2 mm to account for measurement errors) compared to the previous scan. If the tumour size decreased or remained stable after the initial enlargement, the tumour was classified as LC but with ARE. As a tumour with ARE could possibly progress later and be classified as LF, detection of LC/LF and ARE outcome was performed and evaluated independently for each tumour. The outcomes identified automatically were compared with the ground truth outcome for each tumour to evaluate the performance of automatic outcome assessment in terms of accuracy, sensitivity, and specificity.

Figure 3:
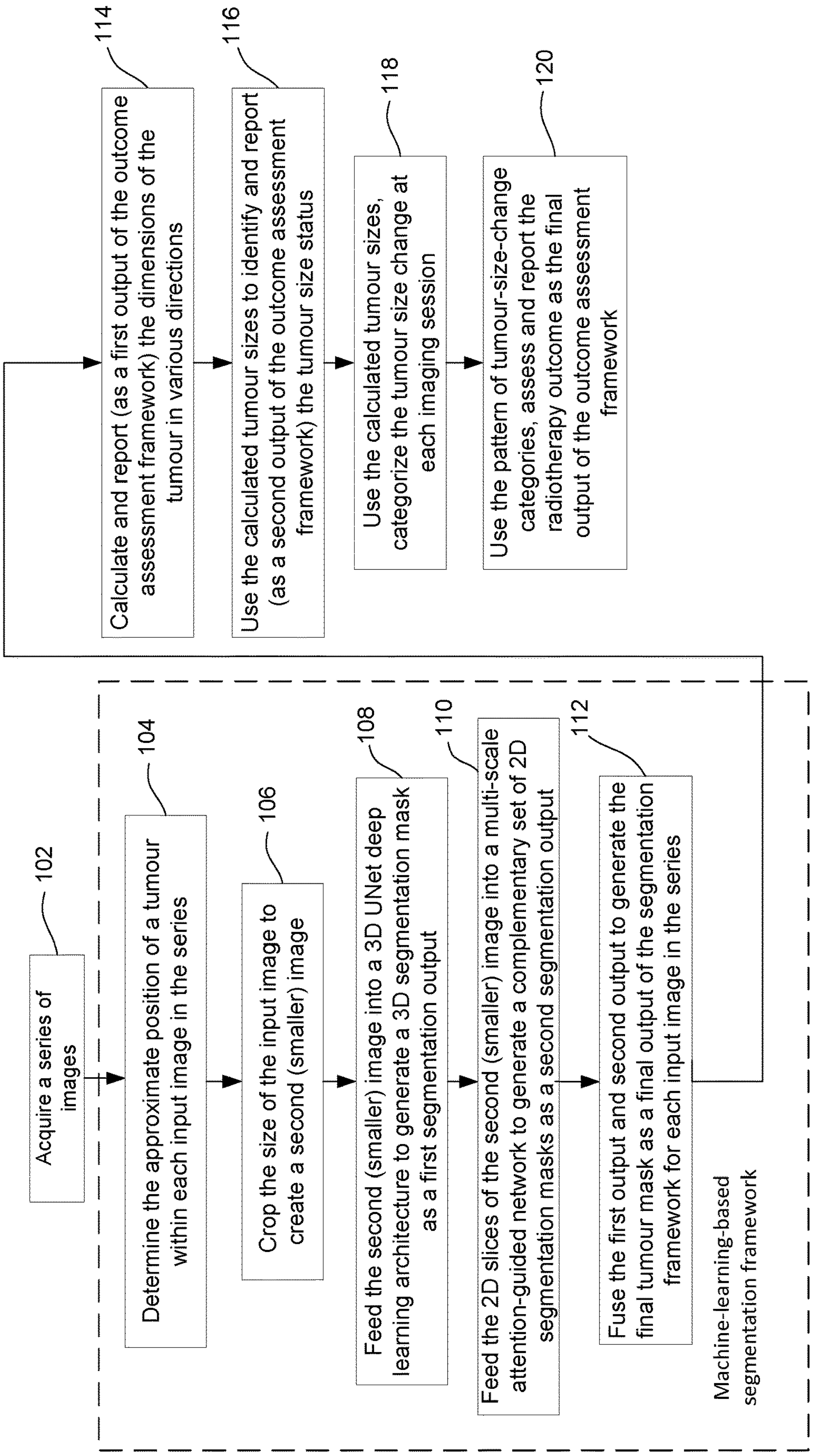
FIG. 3 shows a flowchart with exemplary steps for automatic segmentation of brain tumours and assessment of radiotherapy outcome using serial MRI.

FIG. 3 shows a flowchart 100 with exemplary steps for automatic segmentation of brain tumours on serial MRI and assessment of radiotherapy outcome. In step 102, with an imaging system 14, acquiring a series of input images 12 comprising a region of interest (ROI) comprising a tumour, wherein each of the input images 12 in the series are acquired from the same subject in different imaging sessions before, during and/or after radiotherapy. With a computer system 16 comprising a hardware processor 40 and a memory device 42 on which instructions are encoded to cause the hardware processor 40 to perform the operations of: with a cascade of at least two 2D UNet deep learning models, finding the approximate position of the tumour within each input image in the series (step 104); cropping the size of the input image to create a second (smaller) image without losing any information for tumour segmentation (step 106); feeding the second image into a 3D UNet deep learning architecture to generate a 3D segmentation mask as a first segmentation output (step 108); feeding the 2D slices of the second image into a multi-scale attention-guided network to generate a complementary set of 2D segmentation masks as a second segmentation output (step 110); fusing the first output and second output to generate the final tumour mask as a final output of the segmentation framework for each input image in the series (step 112); calculating and reporting (as a first output of the outcome assessment framework) the dimensions of the tumour in various directions, the longest diameter of tumour in the axial, lateral and coronal planes, the overall longest diameter, the two longest perpendicular diameters of tumour in each of the axial, lateral and coronal planes, and/or the tumour volume at each imaging session using the generated segmentation mask (step 114); using the calculated tumour sizes, identifying and reporting (as a second output of the outcome assessment framework) the tumour size status comprising decrease, stable, increase for each imaging session following clinical guidelines and practice and considering the minimum measurable size on the input images (step 116); using the calculated tumour sizes, categorizing and reporting the tumour size change at each imaging session into three categories of shrinkage, steady and enlargement, based on some predefined criteria such as the RANO criteria and report it as a third output of the outcome assessment framework (step 118); using the pattern of tumour-size-change categories, assessing and reporting the radiotherapy outcome as the final output of the outcome assessment framework, wherein different aspects of radiotherapy outcome to assess comprise complete response/partial response/minor response/stable disease/progressive disease, and/or local control/local failure, and/or adverse radiation effect (yes/no) (step 120).

Results

Figure 4A:
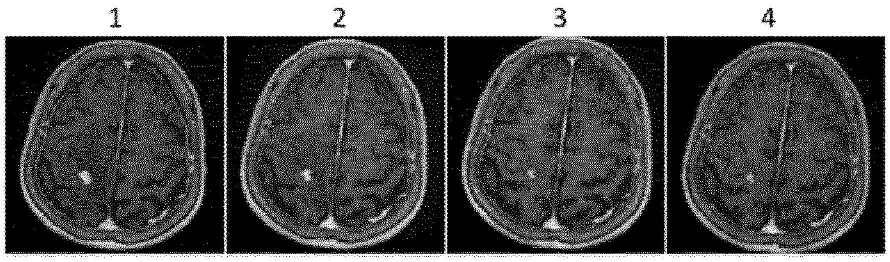
FIG. 4*a* shows contrast-enhanced T1-weighted images acquired at the baseline (1), and the first (2), second (3), and third (4) follow-up sessions after radiotherapy from a first representative patient with brain metastasis demonstrating local control after treatment.
Figure 4B:
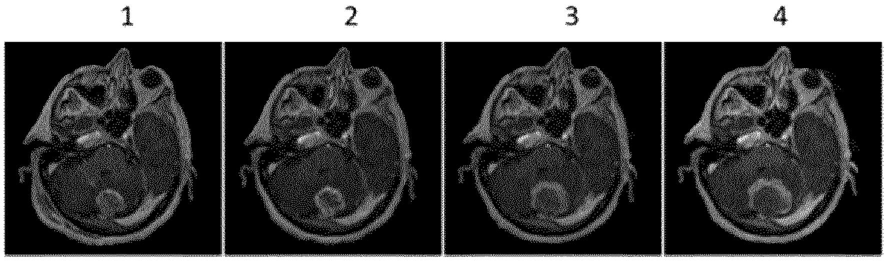
FIG. 4*b* shows contrast-enhanced T1-weighted images acquired at the baseline (1), and the first (2), second (3), and third (4) follow-ups after SRT from a second representative patient with brain metastasis demonstrating local failure after treatment.
Figure 4C:
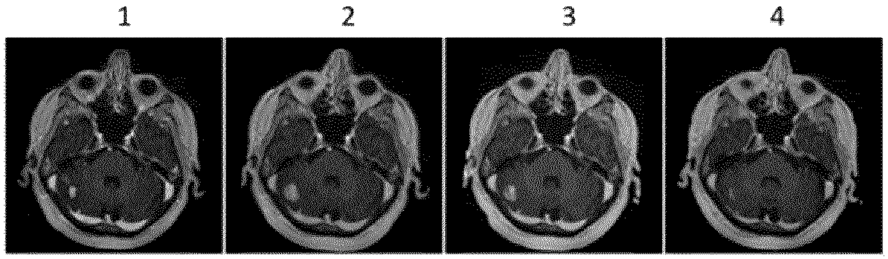
FIG. 4*c* shows contrast-enhanced T1-weighted images acquired at the baseline (1), and the first (2), second (3), and third (4) follow-ups after SRT from a third representative patient with brain metastasis demonstrating ARE after treatment.
Figure 5A:
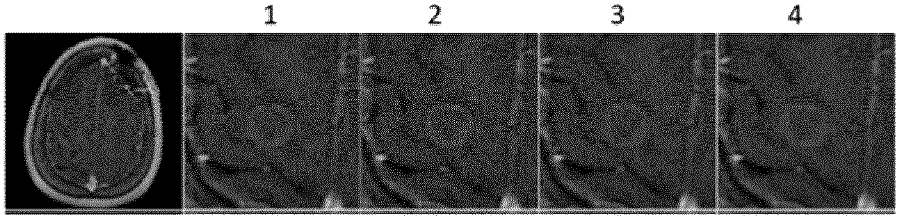
FIGS. 5*a-e* show tumour segmentation masks generated by the cascaded 2D UNets (1), 3D UNet (2), cascaded 2D & 3D UNets (3), and Cascaded 2D & 3D UNets+MSGA (4) for five representative patients (a-e) in the test set.
Figure 5B:
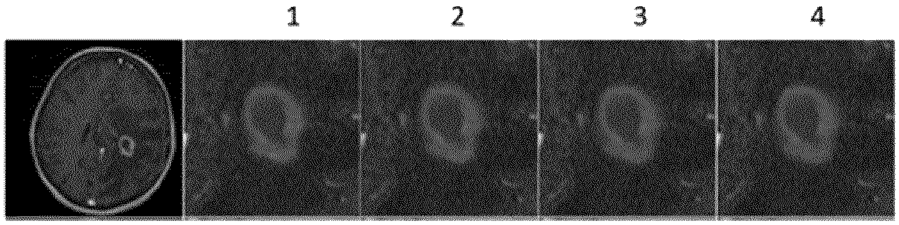
Figure 5C:
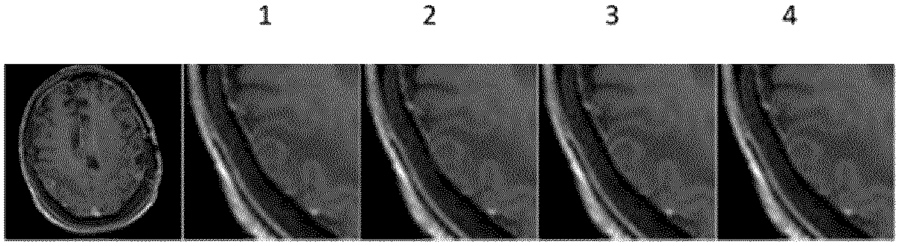
Figure 5D:
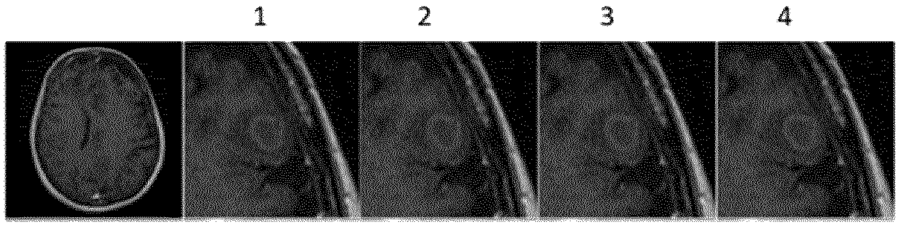
Figure 5E:
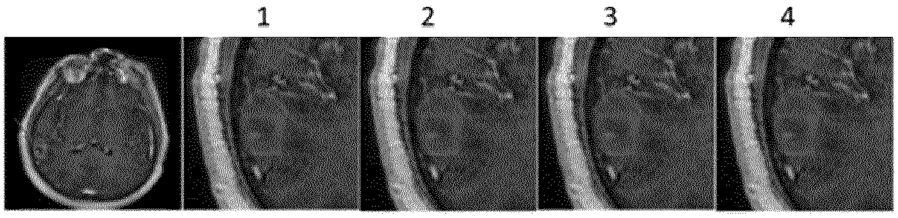

FIGS. 4*a-c* demonstrate contrast-enhanced T1-weighted images acquired form three representative brain metastasis patients with an outcome of LC, LF, and ARE after SRT, respectively. In FIG. 3*a* the tumour has consistently shrunk after SRT (follow-up sessions 1-3), demonstrating an LC outcome. In FIG. 3*b*, the tumour has continued to grow after the first follow-up, showing an LF outcome. In FIG. 3*c*, an initial growth in the first follow-up has stopped immediately in the second follow-up, followed by further shrinkage in the third follow-up, that is an evidence for ARE. The arrow in the baseline image shows the location of brain metastasis. LC/LF/ARE is evaluated based on the changes in longest diameter. In FIG. 3*c* an initial growth in first follow-up is followed by a decrease in the second, and then third follow-ups.

FIGS. 5*a-e* show the ground truth and automatic tumour segmentation masks generated by different deep learning models for five representative patients of the test set. The images show a step-by-step improvement in the automatic segmentation masks generated by the cascaded 2D UNets, 3D UNet, cascaded 2D & 3D UNets, and the complete segmentation framework in this disclosure (cascaded 2D & 3D UNets+MSGA). A detailed comparison between the segmentation results of different networks at the baseline and first follow-up session is given in Table I in terms of dice similarity coefficient, Hausdorff distance, and tumour volume estimation error. A consistent step by step improvement is observed in different criteria of segmentation accuracy, with the best results associated with the cascaded 2D & 3D UNets+MSGA architecture. The networks demonstrate a similar performance of the training and test sets, implying a very good generalizability for tumour segmentation of new unseen cases. Further, the segmentation results are comparable between the baseline and the first follow-up. It should be noted that in the experiments conducted in this study, no data from the first follow-up was used for training the networks. Specifically, the networks were solely trained using data of the training set patients acquired at the baseline but subsequently evaluated using the data acquired at the first follow-up from the patients of the training and test sets, separately.

Table II presents the results of detecting tumour size status at the imaging follow-ups after SRT for patients of the test set using the four different segmentation models. The cascaded 2D & 3D UNets+MSGA architecture demonstrated the best performance with an accuracy of 85.9%. This model without the MSGA component (cascaded 2D & 3D UNets) demonstrated a similar performance in detecting the increase status, but a lower accuracy in detecting the stable and decrease status. Table III reports the results of automatic outcome assessment for the test set patients using the four segmentation models. The results demonstrate that the models with higher accuracy in tumour segmentation and detecting tumour size changes also outperformed the other models in terms of automatic therapy outcome assessment. The framework in this disclosure, in particular, resulted in the best performance with a sensitivity and specificity of 88.9% and 92.3%, respectively, for detecting the LC/LF, and 100% and 89.2% for detecting the ARE outcome.

TABLE I

Dice similarity coefficient (DSC), Hausdorff distance (HD), and volume estimation error (VEE) for segmentation of brain metastasis using different network architectures.

| Segmentation Model | | Baseline Training Set | Baseline Test Set | First Follow-up Training Set Patients | First Follow-up Test Set Patients |
|---|---|---|---|---|---|
| Cascaded 2D UNets | DSC | 86.5 ± 5.8 | 85.4 ± 7 | 82.8 ± 6 | 81.3 ± 5.9 |
| | HD | 2.8 ± 0.4 mm | 3 ± 0.6 mm | 3.2 ± 0.6 mm | 3.7 ± 0.5 mm |
| | VEE | 0.55 ± 0.47 cc | 0.58 ± 0.5 cc | 0.64 ± 0.49 cc | 0.67 ± 0.49 cc |
| | | 15.8% ± 7% | 16.4% ± 9% | 18.3% ± 8.4% | 19.2% ± 8.3% |
| 3D UNet | DSC | 88.5 ± 4.8 | 87.1 ± 5.5 | 84.6 ± 5.5 | 83.6 ± 6.3 |
| | HD | 2.5 ± 0.7 mm | 2.7 ± 0.7 mm | 2.7 ± 0.6 mm | 3.3 ± 0.6 mm |
| | VEE | 0.52 ± 0.42 cc | 0.53 ± 0.45 cc | 0.58 ± 0.5 cc | 0.61 ± 0.48 cc |
| | | 15% ± 5.4% | 15.4% ± 7% | 17.7% ± 6.4% | 17.8% ± 9.1% |
| Cascaded 2D & 3D UNets | DSC | 90.1 ± 4.4 | 89.6 ± 4.6 | 86.2 ± 4.6 | 85.1 ± 5 |
| | HD | 2.3 ± 0.2 mm | 2.4 ± 0.4 mm | 2.6 ± 0.5 mm | 3.1 ± 0.8 mm |
| | VEE | 0.5 ± 0.32 cc | 0.51 ± 0.4 cc | 0.55 ± 0.43 cc | 0.57 ± 0.48 cc |
| | | 11.1% ± 4.2% | 12.5% ± 5.3% | 16.7% ± 8.3% | 18.2% ± 8% |
| Cascaded 2D & 3D UNets + MSGA | DSC | 92.3 ± 3.1 | 91.5 ± 3.7 | 88.7 ± 3.7 | 87.4 ± 5.2 |
| | HD | 1.84 ± 0.4 mm | 2.1 ± 0.6 mm | 2.21 ± 0.5 mm | 2.84 ± 0.7 mm |
| | VEE | 0.39 ± 0.32 cc | 0.44 ± 0.36 cc | 0.52 ± 0.4 cc | 0.57 ± 0.5 cc |
| | | 9.2% ± 4.6% | 10.2% ± 5.3% | 12.5% ± 4% | 13.4% ± 5.1% |

TABLE II

Results of detecting tumour size status at follow-up sessions after SRT for the patients of test set using different segmentation models.

| Segmentation Model | Tumour Size Status | Accuracy | Precision | Recall |
|---|---|---|---|---|
| Cascaded 2D UNets | Increase | 71.8% | 82.3% | 70% |
| | Stable | | 57.6% | 82.6% |
| | Decrease | | 92.8% | 62.9% |
| 3D UNet | Increase | 79.6% | 85% | 85% |
| | Stable | | 67.9% | 82.6% |
| | Decrease | | 93% | 71.4% |
| Cascaded 2D & 3D UNets | Increase | 82.8% | 90% | 90% |
| | Stable | | 70% | 91.3% |
| | Decrease | | 100% | 66.7% |
| Cascaded 2D & 3D UNets + MSGA | Increase | 85.9% | 90% | 90% |
| | Stable | | 75% | 91.3% |
| | Decrease | | 100% | 76.2% |

TABLE III

Results of detecting the LC/LF and ARE outcomes for the patients of test set based on the RANO-BM criteria using different segmentation models.

| Segmentation Model | LC/LF Detection Accuracy | LC/LF Detection Sensitivity | LC/LF Detection Specificity | ARE Detection Accuracy | ARE Detection Sensitivity | ARE Detection Specificity |
|---|---|---|---|---|---|---|
| Cascaded 2D UNets | 72.7% | 66.67% | 76.9% | 77.2% | 66.7% | 79% |
| 3D UNet | 81.9% | 77.8% | 84.6% | 81.9% | 66.7% | 84.2% |
| Cascaded 2D & 3D UNets | 86.3% | 77.8% | 92.3% | 86.4% | 100% | 84.2% |
| Cascaded 2D & 3D UNets + MSGA | 90.9% | 88.9% | 92.3% | 90.9% | 100% | 89.2% |

The exemplary segmentation framework developed in the study described in [0032] was designed such that it can tackle the memory limitations associated with effective training of complex deep networks by cropping the volumetric images around the tumour. Two cascaded 2D UNets were trained to find the approximate position of the tumour. This position is later used to crop the MRI volume around the tumour. Experimental results show that whereas the cascaded 2D UNets and the 3D UNet alone had an average dice similarity coefficient of 85.4 and 87.1 and Hausdorff distance of 3 and 2.7 mm, respectively, on the test set, the cascaded 2D & 3D UNet model could considerably improve the segmentation accuracy and resulted in an average dice similarity coefficient of 89.6 and Hausdorff distance of 2.4 mm.

The exemplary segmentation framework developed in the study described in [0032] outperformed the cascaded 2D UNets, the 3D UNet, and the cascaded 2D & 3D Unet models with an average dice score of 91.5 and volume estimation error of 0.44 cc on the independent test set at the baseline, compared to 85.4 and 0.58 cc, 87.1 and 0.53 cc, and 89.6 and 0.51 cc respectively. By incorporating the MSGA network into the framework, the model benefits from both the cascading and ensembling mechanisms to improve the segmentation accuracy [31]. The MSGA network applies a multi-scale attention mechanism to focus on crucial regions of the images and discard redundancies in the extracted features while learning tumour segmentation. Also, complementary information is provided to the framework through MSGA by feeding T2-FLAIR images as an additional input channel to the MSGA network. As such, fusing the outcome of this network with the 3D UNet potentially improves the overall performance of the segmentation framework, as observed in this study.

Performance of the exemplary framework developed in the study described in [0032] was subsequently evaluated in monitoring the tumour size status at several imaging follow-ups after SRT. Experimental results demonstrated an accuracy of 86% with a precision and recall of 90% and 90%, 75% and 91%, and 100% and 76% in detecting increase, stable and decrease statuses, respectively, on the independent test. It should be noted though, these labels were manually determined at each follow-up by only one observer and therefore labelling error is expectable due to measurement errors, specially for smaller tumours and those lying closer to the class boundaries. Such errors may affect the reported accuracies in automatic labeling of the tumour size status. Future studies may mitigate possible errors in ground truth labeling of tumour size status using a multiple observer strategy.

The exemplary framework developed in the study described in [0032] also demonstrated a promising performance in automatic assessment of SRT outcome with an accuracy, sensitivity, and specificity of 91%, 89%, 92%, respectively, in detecting LC/LF and 91%, 100%, and 89% for ARE detection on the independent test set. The automatic outcome assessment framework in this study evaluates the presence of ARE after radiotherapy based on the pattern of changes in tumour size on serial MRI, with an acceptable accuracy. However, it should be noted that monitoring tumour size changes on serial imaging is not always enough to draw an accurate conclusion on whether an observed tumour size increase on imaging is associated with progressive disease or ARE. Along with other radiological insights such as those based on T1/T2 matching or use of perfusion MRI [15], [32], additional clinical evidence including histological confirmation is sometimes required to diagnose ARE. As such, standard serial MRI is usually used by oncologists in conjunction with other clinical criteria to detect pseudo-progression or radiation necrosis after radiotherapy.

The exemplary segmentation framework developed in the study described in [0032] demonstrated a good generalizability in longitudinal segmentation of brain tumours on serial MRI, while it was only trained on the baseline images of the training set. The generalizability of the framework makes it an appropriate fit for the task of automatic therapy outcome assessment. As such, this disclosure describes a novel framework comprising a deep learning-based segmentation model adapted for automatic assessment of radiotherapy outcome in brain metastasis, which overcomes the deficiencies of prior art methods and systems. With the high volume of imaging data acquired for these patients, such automatic framework can streamline radiation therapy workflow considerably and facilitates precision oncology by regular and high-throughput response assessment. While the results presented in this work is encouraging and paves the way for future studies, more investigations are required for further evaluation of the methodologies on larger patient populations and possibly multi-centre imaging data.

In yet another implementation, a tensor processing unit (TPU) may be employed as an alternative to the GPU 41, which allows for the model to be run in a substantially faster and smoother manner. A TPU is an AI accelerator application-specific integrated circuit (ASIC) specifically for neural network machine learning.

Implementations of the subject matter and the functional operations described in this specification can be implemented in digital electronic circuitry, in tangibly embodied computer software or firmware, in computer hardware, including the structures disclosed in this specification and their structural equivalents, or in combinations of one or more of them. Implementations of the subject matter described in this specification can be implemented as one or more computer programs, i.e., one or more modules of computer program instructions encoded on a tangible, non-transitory computer-storage medium for execution by, or to control the operation of, data processing apparatus. Alternatively or in addition, the program instructions can be encoded on an artificially generated propagated signal, e.g., a machine-generated electrical, optical, or electromagnetic signal that is generated to encode information for transmission to suitable receiver apparatus for execution by a data processing apparatus. The computer-storage medium can be a machine-readable storage device, a machine-readable storage substrate, a random or serial access memory device, or a combination of one or more of them.

A computer program, which may also be referred to or described as a program, software, a software application, a module, a software module, a script, or code can be written in any form of programming language, including compiled or interpreted languages, or declarative or procedural languages, and it can be deployed in any form, including as a stand-alone program or as a module, component, subroutine, or other unit suitable for use in a computing environment. A computer program may, but need not, correspond to a file in a file system. A program can be stored in a portion of a file that holds other programs or data, e.g., one or more scripts stored in a markup language document, in a single file dedicated to the program in question, or in multiple coordinated files, e.g., files that store one or more modules, sub-programs, or portions of code. A computer program can be deployed to be executed on one computer or on multiple computers that are located at one site or distributed across multiple sites and interconnected by a communication network. While portions of the programs illustrated in the various figures are shown as individual modules that implement the various features and functionality through various objects, methods, or other processes, the programs may instead include a number of sub-modules, third-party services, components, libraries, and such, as appropriate. Conversely, the features and functionality of various components can be combined into single components, as appropriate.

The processes and logic flows described in this specification can be performed by one or more programmable computers executing one or more computer programs to perform functions by operating on input data and generating output. The processes and logic flows can also be performed by, and apparatus can also be implemented as, special purpose logic circuitry, e.g., a CPU, a GPU, an FPGA, or an ASIC.

To provide for interaction with a user, implementations of the subject matter described in this specification can be implemented on a computer having a display device, e.g., a CRT (cathode ray tube), LCD (liquid crystal display), LED (Light Emitting Diode), or plasma monitor, for displaying information to the user and a keyboard and a pointing device, e.g., a mouse, trackball, or trackpad by which the user can provide input to the computer. Input may also be provided to the computer using a touchscreen, such as a tablet computer surface with pressure sensitivity, a multi-touch screen using capacitive or electric sensing, or other type of touchscreen. Other kinds of devices can be used to provide for interaction with a user as well; for example, feedback provided to the user can be any form of sensory feedback, e.g., visual feedback, auditory feedback, or tactile feedback; and input from the user can be received in any form, including acoustic, speech, or tactile input.

The term "graphical user interface," or "GUI," may be used in the singular or the plural to describe one or more graphical user interfaces and each of the displays of a particular graphical user interface. Therefore, a GUI may represent any graphical user interface, including but not limited to, a web browser, a touch screen, or a command line interface (CLI) that processes information and efficiently presents the information results to the user. In general, a GUI may include a plurality of user interface (UI) elements, some or all associated with a web browser, such as interactive fields, pull-down lists, and buttons operable by the user. These and other UI elements may be related to or represent the functions of the web browser.

Implementations of the subject matter described in this specification can be implemented in a computing system that includes a back-end component, e.g., as a data server, or that includes a middleware component, e.g., an application server, or that includes a front-end component, e.g., a client computer having a graphical user interface or a Web browser through which a user can interact with an implementation of the subject matter described in this specification, or any combination of one or more such back-end, middleware, or front-end components. The components of the system 10 can be interconnected by any form or medium of wireline and/or wireless digital data communication, e.g., a communications network 44. Examples of communication networks include a local area network (LAN), a radio access network (RAN), a metropolitan area network (MAN), a wide area network (WAN), Worldwide Interoperability for Microwave Access (WIMAX), a wireless local area network (WLAN) using, for example, 802.11 a/b/g/n and/or 802.20, all or a portion of the Internet, and/or any other communication system or systems at one or more locations, and free-space optical networks. The network may communicate with, for example, Internet Protocol (IP) packets, Frame Relay frames, Asynchronous Transfer Mode (ATM) cells, voice, video, data, and/or other suitable information between network addresses.

The computing system can include clients and servers and/or Internet-of-Things (IoT) devices running publisher/subscriber applications. A client and server are generally remote from each other and typically interact through a communication network. The relationship of client and server arises by virtue of computer programs running on the respective computers and having a client-server relationship to each other.

There may be any number of computers associated with, or external to, the system 10 and communicating over network 44. Further, the terms "client," "user," and other appropriate terminology may be used interchangeably, as appropriate, without departing from the scope of this disclosure.

In another implementation, system 10 follows a cloud computing model, by providing an on-demand network access to a shared pool of configurable computing resources (e.g., servers, storage, applications, and/or services) that can be rapidly provisioned and released with mini-mal or nor resource management effort, including interaction with a service provider, by a user (operator of a thin client).

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hard-ware and computer instructions.

Benefits, other advantages, and solutions to problems have been described above with regard to specific embodiments. However, the benefits, advantages, solutions to problems, and any element(s) that may cause any benefit, advantage, or solution to occur or become more pronounced are not to be construed as critical, required, or essential features or elements of any or all the claims. As used herein, the terms "comprises," "comprising," or any other variations thereof, are intended to cover a non-exclusive inclusion, such that a process, method, article, or apparatus that comprises a list of elements does not include only those elements but may include other elements not expressly listed or inherent to such process, method, article, or apparatus. Further, no element described herein is required for the practice of the invention unless expressly described as "essential" or "critical."

The preceding detailed description of exemplary embodiments of the invention makes reference to the accompanying drawings, which show the exemplary embodiment by way of illustration. While these exemplary embodiments are described in sufficient detail to enable those skilled in the art to practice the invention, it should be understood that other embodiments may be realized and that logical and mechanical changes may be made without departing from the spirit and scope of the invention. For example, the steps recited in any of the method or process claims may be executed in any order and are not limited to the order presented. Thus, the preceding detailed description is presented for purposes of illustration only and not of limitation, and the scope of the invention is defined by the preceding description, and with respect to the attached claims.

REFERENCES

[1] R. M. Auchter et al., "A multiinstitutional outcome and prognostic factor analysis of radiosurgery for resectable single brain metastasis," *Int. J. Radiat. Oncol.*, vol. 35, no. 1, pp. 27-35. April 1996, doi: 10.1016/S0360-3016(96)85008-5.

[2] B. D. Fox, V. J. Cheung, A. J. Patel, D. Suki, and G. Rao, "Epidemiology of Metastatic Brain Tumours," *Neurosurg. Clin. N. Am.*, vol. 22, no. 1, pp. 1-6, January 2011, doi: 10.1016/j.nec.2010.08.007.

[3] C. Nieder, O. Spanne, M. P. Mehta, A. L. Grosu, and H. Geinitz, "Presentation, patterns of care, and survival in patients with brain metastases," *Cancer*, vol. 117, no. 11, pp. 2505-2512 June 2011, doi: 10.1002/cncr.25707.

[4] R. L. Siegel, K. D. Miller, and A. Jemal, "Cancer statistics, 2019," *CA. Cancer J. Clin.*, vol. 69, no. 1, pp. 7-34, January 2019, doi: 10.3322/caac.21551.

[5] P. W. Sperduto et al., "Estimating Survival in Patients With Lung Cancer and Brain Metastases," *JAMA Oncol.*, vol. 3, no. 6, p. 827, June 2017, doi: 10.1001/jamaoncol.2016.3834.

[6] P. W. Sperduto et al., "Estimating survival in patients with gastrointestinal cancers and brain metastases: An update of the graded prognostic assessment for gastrointestinal cancers (GI-GPA)," *Clin. Transl. Radiat. Oncol.*, vol. 18, pp. 39-45, September 2019, doi: 10.1016/j.ctro.2019.06.007.

[7] D. N. Cagney et al., "Incidence and prognosis of patients with brain metastases at diagnosis of systemic malignancy: a population-based study," *Neuro. Oncol.*, vol. 19, no. 11, pp. 1511-1521 October 2017, doi: 10.1093/neuonc/nox077.

[8] P. W. Sperduto et al., "Estimating Survival in Melanoma Patients With Brain Metastases: An Update of the Graded Prognostic Assessment for Melanoma Using Molecular Markers (Melanoma-molGPA)," *Int. J. Radiat. Oncol.*, vol. 99, no. 4, pp. 812-816. November 2017, doi: 10.1016/j.ijrobp.2017.06.2454.

[9] T. K. Owonikoko et al., "Current approaches to the treatment of metastatic brain tumours," vol. 11, no. 4, pp. 203-222, 2014, doi: 10.1038/nrclinonc.2014.25.Current.

[10] P. D. Brown, M. S. Ahluwalia, O. H. Khan, A. L. Asher, J. S. Wefel, and V. Gondi, "Whole-brain radiotherapy for brain metastases: Evolution or revolution?," *Journal of Clinical Oncology*, vol. 36, no. 5. pp. 483-491, 2018, doi: 10.1200/JCO.2017.75.9589.

[11] Chukwueke U N, Wen P Y. Use of the Response Assessment in Neuro-Oncology (RANO) criteria in clinical trials and clinical practice. CNS Oncol. 2019 Mar. 1; 8(1):CNS28. doi: 10.2217/cns-2018-0007. Epub 2019 Feb. 26. PMID: 30806082.

[12] N. U. Lin et al., "Response assessment criteria for brain metastases: proposal from the RANO group," *Lancet. Oncol.*, vol. 16, no. 6, pp. e270-8, June 2015, doi: 10.1016/S1470-2045(15)70057-4.

[13] P. K. Sneed et al., "Adverse radiation effect after stereotactic radiosurgery for brain metastases: incidence, time course, and risk factors," *J. Neurosurg.*, vol. 123, no. 2, pp. 373-86, August 2015, doi: 10.3171/2014.10.JNS141610.

[14] M. T. Truong et al., "Results of surgical resection for progression of brain metastases previously treated by gamma knife radiosurgery," *Neurosurgery*, vol. 59, no. 1, pp. 86-97; discussion 86-97, July 2006, doi: 10.1227/01.NEU.0000219858.80351.38.

[15] H. Kano, D. Kondziolka, J. Lobato-Polo, O. Zorro, J. C. Flickinger, and L. D. Lunsford, "T1/T2 matching to differentiate tumour growth from radiation effects after stereotactic radiosurgery," *Neurosurgery*, vol. 66, no. 3, pp. 486-91; discussion 491-2, March 2010, doi: 10.1227/01.NEU.0000360391.35749.A5.

[16] E. Karami et al., "Quantitative MRI Biomarkers of Stereotactic Radiotherapy Outcome in Brain Metastasis.," *Sci. Rep.*, vol. 9, p. 19830, December 2019, doi: 10.1038/s41598-019-56185-5.

[17] A. Tiwari, S. Srivastava, and M. Pant, "Brain tumour segmentation and classification from magnetic resonance images: Review of selected methods from 2014 to 2019," *Pattern Recognit. Lett.*, vol. 131, pp. 244-260, March 2020, doi: 10.1016/j.patrec.2019.11.020.

[18] Z. Liu et al., "Deep Learning Based Brain Tumour Segmentation: A Survey," July 2020.

[19] N. Gordillo, E. Montseny, and P. Sobrevilla, "State of the art survey on MRI brain tumour segmentation," *Magn. Reson. Imaging*, vol. 31, no. 8, pp. 1426-1438, 2013, doi: 10.1016/j.mri.2013.05.002.

[20] A. Jalalifar, H. Soliman, M. Ruschin, A. Sahgal, and A. Sadeghi-Naini, "A Brain Tumour Segmentation Framework Based on Outlier Detection Using One-Class Support Vector Machine," in 2020 42*nd Annual International Conference of the IEEE Engineering in Medicine & Biology Society* (*EMBC*), July 2020, pp. 1067-1070, doi: 10.1109/EMBC44109.2020.9176263.

[21] E. Karami et al., "An Automatic Framework for Segmentation of Brain Tumours at Follow-up Scans after Radiation Therapy *," in 2019 41*st Annual International Conference of the IEEE Engineering in Medicine and Biology Society* (*EMBC*), July 2019, pp. 463-466, doi: 10.1109/EMBC.2019.8856858.

[22] X. Zhao, Y. Wu, G. Song, Z. Li, Y. Zhang, and Y. Fan, "A deep learning model integrating FCNNs and CRFs for brain tumour segmentation," *Med. Image Anal.*, vol. 43, pp. 98-111, January 2018, doi: 10.1016/j.media.2017.10.002.

[23] M. Havaei et al., "Brain tumour segmentation with Deep Neural Networks," *Med. Image Anal.*, vol. 35, pp. 18-31, January 2017, doi: 10.1016/j.media.2016.05.004.

[24] A. Işin, C. Direkoğlu, and M. Şah, "Review of MRI-based Brain Tumour Image Segmentation Using Deep Learning Methods," *Procedia Comput. Sci.*, vol. 102, pp. 317-324, 2016, doi: 10.1016/j.procs.2016.09.407.

[25] Z. Zhou, M. M. R. Siddiquee, N. Tajbakhsh, and J. Liang, "UNet++: A Nested U-Net Architecture for Medical Image Segmentation," July 2018.

[26] Ö. Çiçek, A. Abdulkadir, S. S. Lienkamp, T. Brox, and O. Ronneberger, "3D U-Net; Learning Dense Volumetric Segmentation from Sparse Annotation," June 2016.

[27] H. Dong, G. Yang, F. Liu, Y. Mo, and Y. Guo, "Automatic Brain Tumour Detection and Segmentation Using U-Net Based Fully Convolutional Networks," pp. 1-12, 2017, doi: 10.1007/978-3-319-60964-5_44.

[28] O. Ronneberger, P. Fischer, and T. Brox, "U-Net: Convolutional Networks for Biomedical Image Segmentation," in *Medical Image Computing and Computer-Assisted Intervention* (*MICCAI*), 2015, pp. 234-241, doi: 10.1007/978-3-319-24574-4_28.

[29] A. Sinha and J. Dolz, "Multi-scale guided attention for medical image segmentation," June 2019.

[30] B. H. Menze et al., "The Multimodal Brain Tumour Image Segmentation Benchmark (BRATS)," *IEEE Trans. Med. Imaging*, vol. 34, no. 10, pp. 1993-224 October 2015, doi: 10.1109/TMI.2014.2377694.

[31] O. Sagi and L. Rokach, "Ensemble learning: A survey," *Wiley Interdiscip. Rev. Data Min. Knowl. Discov.*, vol. 8, no. 4, July 2018, doi: 10.1002/widm.1249.

[32] B. Vellayappan et al., "Diagnosis and Management of Radiation Necrosis in Patients With Brain Metastases.," *Front. Oncol.*, vol. 8, p. 395, 2018, doi: 10.3389/fonc.2018.00395.

The invention claimed is:

1. A system for automatic assessment of therapy outcome in cancer patients treated with radiation therapy, the system comprising:

an imaging system for acquiring a series of input images comprising a region of interest (ROI) comprising a tumour, wherein each of the input images in the series is acquired from a same subject in different imaging sessions before, during and/or after the radiation therapy;

a computer system comprising a hardware processor and a memory device on which instructions are encoded to cause the hardware processor to perform operations of:

with a machine-learning-based segmentation framework comprising one deep neural network or a plurality of deep neural networks in cascade and/or parallel configurations, generating at least a tumour mask as a final output of the segmentation framework for each input image in the series;

calculating and reporting dimensions of the tumour in various directions;

using the calculated tumour dimensions, identifying and reporting a tumour size status;

using the calculated tumour dimensions, categorizing and reporting a tumour size change at each imaging session of the different imaging sessions into categories comprising at least one of shrinkage, steady and enlargement, based on a predefined criteria comprising at least a response assessment in neuro-oncology (RANO) criteria;

using a pattern of the tumour-size-change categories across the different imaging sessions, automatically assessing and reporting the radiation therapy-specific outcome comprising at least one of local control, local failure, or presence or absence of adverse radiation effect.

2. The system of claim 1, wherein the automatic assessment of radiation therapy outcome in tumours uses magnetic resonance imaging (MRI).

3. The system of claim 1, wherein the imaging system is a magnetic resonance imaging (MRI) and wherein a deep learning-based segmentation model delineates tumours longitudinally on serial MRI.

4. The system of claim 3, comprising training the framework using data acquired from a plurality of patients and evaluated on an independent test set of patients.

5. The system of claim 1, wherein the machine learning-based segmentation framework comprises at least one of a deep convolutional neural network (DCNN) architecture, or a deep learning architecture.

6. The system of claim 5, wherein a size of each of the input images is 512×512×128 voxel.

7. The system of claim 5, wherein the system is configured to analyze longitudinal changes in tumour size to assess a local response and detect possible adverse radiation effects (ARE) after stereotactic radiation therapy (SRT).

8. The system of claim 1, wherein the dimensions of the tumour in various directions comprise at least one of longest diameter of the tumour in axial, lateral and coronal planes, overall longest diameter, two longest perpendicular diameters of tumour in each of the axial, lateral and coronal planes, and/or the tumour volume at each imaging session using the generated segmentation mask.

9. The system of claim 1, further comprising operations of using the calculated tumour dimensions, identifying and reporting the tumour size status comprising at least one of decrease, stable, increase for each imaging session of the different imaging sessions following clinical guidelines and practice and considering a minimum measurable size on the input images.

10. The system of claim 1, wherein the radiation therapy outcome comprises at least one of a complete response/partial response/minor response/stable disease/progressive disease, and/or local control/local failure, and/or a presence or absence of adverse radiation effect.

11. A method for automatic assessment of therapy outcome in cancer patients treated with radiation therapy, the method comprising:

with an imaging system, acquiring a series of input images comprising a region of interest (ROI) comprising a tumour, wherein each of the input images in the series are acquired from a same subject in different imaging sessions before, during and/or after the radiation therapy;

with a machine-learning-based segmentation framework comprising one deep neural network or a plurality of deep neural networks in cascade and/or parallel configurations, generating at least a tumour mask as a final output of the segmentation framework for each input image in the series;

calculating and reporting dimensions of the tumour in various directions;

using the calculated tumour dimensions, identifying and reporting a tumour size status;

using the calculated tumour dimensions, categorizing and reporting the tumour size change at each mentioned imaging session into categories comprising at least one of shrinkage, steady and enlargement, based on a predefined criteria comprising at least a response assessment in neuro-oncology (RANO) criteria;

using a pattern of the tumour-size-change categories across the different imaging sessions, automatically assessing and reporting the radiation-specific therapy outcome comprising at least one of local control, local failure, or presence or absence of adverse radiation effect.

12. The method of claim 11, wherein the automatic assessment of radiation therapy outcome in tumours uses magnetic resonance imaging (MRI).

13. The method of claim 11, wherein the imaging system is a magnetic resonance imaging (MRI) and wherein a deep learning-based segmentation model delineates tumours longitudinally on serial MRI.

14. The method of claim 13, further comprising training the framework using data acquired from a plurality of patients and evaluated on an independent test set of patients.

15. The method of claim 13, wherein longitudinal changes in tumour size are analyzed automatically to assess a local response and detect possible adverse radiation effects (ARE) after stereotactic radiation therapy (SRT).

16. The method of claim 11, wherein the machine learning-based segmentation framework comprises at least one of a deep convolutional neural network (DCNN) architecture, or a deep learning architecture.

17. The method of claim 11, wherein the dimensions of the tumour in various directions comprise at least one of longest diameter of the tumour in axial, lateral and coronal planes, overall longest diameter, two longest perpendicular diameters of tumour in each of the axial, lateral and coronal planes, and/or the tumour volume at each imaging session using the generated segmentation mask.

18. The method of claim 11, further comprising steps of using the calculated tumour dimensions, identifying and reporting a tumour size status comprising at least one of decrease, stable, increase for each imaging session of the different imaging sessions following clinical guidelines and practice and considering a minimum measurable size on the input images.

19. The method of claim 11, wherein the radiation therapy outcome comprises at least one of a complete response/partial response/minor response/stable disease/progressive disease, and/or local control/local failure, and/or a presence or absence of adverse radiation effect.

20. A computer readable medium storing instructions executable by a processor to carry out operations comprising:

receiving a series of input images comprising a region of interest (ROI) comprising a tumour, wherein each of the input images in the series are acquired from a same subject in different imaging sessions before, during and/or after radiation therapy;

with a machine-learning-based segmentation framework comprising one deep neural network or a plurality of deep neural networks in cascade and/or parallel configurations, generating at least a tumour mask as a final output of the segmentation framework for each input image in the series;

calculating and reporting dimensions of the tumour in various directions;

using the calculated tumour dimensions, identifying and reporting a tumour size status;

using the calculated tumour dimensions, categorizing and reporting a tumour size change at each imaging session of the different imaging sessions into categories comprising at least one of shrinkage, steady and enlargement, based on a predefined criteria comprising at least a response assessment in neuro-oncology (RANO) criteria;

using a pattern of the tumour-size-change categories across the different imaging sessions, automatically assessing and reporting the radiation-specific therapy outcome comprising at least one of local control, local failure, or presence or absence of adverse radiation effect.

21. The computer readable medium of claim 20, wherein the assessment of radiation therapy outcome in tumours uses magnetic resonance imaging (MRI).

22. The computer readable medium of claim 20, wherein a deep learning-based segmentation model is used to delineate tumours longitudinally on serial magnetic resonance imaging (MRI).

23. The computer readable medium of claim 20, comprising a further step of training the framework using data acquired from a plurality of patients and evaluated on an independent test set of patients.

24. The computer readable medium of claim 20, wherein the machine-learning-based segmentation framework comprises at least one of a deep convolutional neural network (DCNN) architecture, or a deep learning architecture.

25. The computer readable medium of claim 20, wherein longitudinal changes in tumour size are analyzed automatically to assess a local response and detect possible adverse radiation effects (ARE) after stereotactic radiation therapy (SRT).

26. The computer readable medium of claim 20, wherein the dimensions of the tumour in various directions comprise at least one of longest diameter of the tumour in axial, lateral and coronal planes, overall longest diameter of the tumour, two longest perpendicular diameters of the tumour in each of the axial, lateral and coronal planes, and/or the tumour volume at each imaging session using the generated segmentation mask.

27. The computer readable medium of claim 20, further comprising steps of using the calculated tumour dimensions, identifying and reporting the tumour size status comprising at least one of decrease, stable, increase for each imaging session following clinical guidelines and practice and considering a minimum measurable size on the input images.

28. The computer readable medium of claim 20, wherein the radiation therapy outcome comprises at least one of a complete response/partial response/minor response/stable disease/progressive disease, and/or local control/local failure, and/or a presence or absence of adverse radiation effect.

* * * * *